(12) United States Patent
Schur et al.

(10) Patent No.: US 7,422,909 B2
(45) Date of Patent: Sep. 9, 2008

(54) HARSH ENVIRONMENT GAS SENSOR APPARATUS AND METHOD

(75) Inventors: Henry B. Schur, Hallandale Beach, FL (US); Jennifer Schur, Hallandale Beach, FL (US); Gary Morgan, Ft. Lauderdale, FL (US)

(73) Assignee: Acme Technologies, Inc, Fort Lauderdale, FL (US)

( * ) Notice: Subject to any disclaimer, the term of this patent is extended or adjusted under 35 U.S.C. 154(b) by 896 days.

(21) Appl. No.: 10/769,898

(22) Filed: Feb. 2, 2004

(65) Prior Publication Data

US 2005/0170520 A1    Aug. 4, 2005

(51) Int. Cl.
*G01N 1/00* (2006.01)
(52) U.S. Cl. .................................................... 436/177
(58) Field of Classification Search .................. 436/177
See application file for complete search history.

(56) References Cited

U.S. PATENT DOCUMENTS

| | | | |
|---|---|---|---|
| 4,664,886 A | | 5/1987 | Novack et al. |
| 5,010,021 A | | 4/1991 | Bell et al. |
| 5,155,357 A | * | 10/1992 | Hemond ..................... 250/291 |
| 5,226,314 A | * | 7/1993 | Baret .......................... 73/40.7 |
| 5,425,268 A | | 6/1995 | Li et al. |
| 5,525,799 A | * | 6/1996 | Andresen et al. ............. 250/288 |
| 5,980,832 A | * | 11/1999 | Andresen et al. .............. 422/91 |
| 5,981,289 A | | 11/1999 | Wright et al. |
| D432,037 S | | 10/2000 | Worth et al. |
| 6,198,400 B1 | | 3/2001 | Church et al. |

* cited by examiner

*Primary Examiner*—Walter D. Griffin
*Assistant Examiner*—Bobby Ramdhanie
(74) *Attorney, Agent, or Firm*—Robert J. Van Der Wall

(57) ABSTRACT

Provided is an apparatus for gas sampling from a harsh environment which comprises a chemically resistant plastic housing suitable for suspension in a confined spacial environment. The housing has apertures for inlet and outlet tubes by which sampled air is drawn into and then discharged from the housing. Included are two three way valves to control selective fluid communication with the environment, a gas sensor, a filter selectively remove contamination from the housing and prevent saturation of the gas sensor, a pump disposed within the housing to effect selective fluid flow through the gas sensor and filter, and a power source that is preferably batteries.

The apparatus electronics are all integrated into an electronics module configured so as to communicate with an external readout in a remote location via several methods. Sampling data is accumulated by a data logger which includes the capacity to retain such information as date and time of sampling, concentration of each sample, and the unit's identification data. The electronics module is in electrical communication with the power source. Power is also supplied to the pump and valves that control the admission of sample gas, direction of it to the sensor, discharge of gas to the harsh environment, and filtration of all the atmosphere within the housing to (1) flush the sensor and (2) clear contamination from the interior of the housing.

15 Claims, 2 Drawing Sheets

HARSH ENVIRONMENT GAS SENSOR APPARATUS AND METHOD

BACKGROUND OF THE INVENTION

1. Field of the Invention

The present invention generally relates to the field of remote continuing discrete monitoring of particular substances, and more particularly to a apparatus for the sensing of gases in harsh environments such as, but not limited to, hydrogen sulfide gas on a continuing discrete basis, and the communication of that information remotely. It also relates to the method of operation of that apparatus.

2. Description of the Prior Art

Exposure to hazardous gases in confined spaces has been recognized as a major danger for many years for both personnel required to enter such spaces and the damaging effect the gases have on the equipment and materials exposed to the gases and their chemical byproducts. The latter condition is generally referred to herein as a harsh environment.

Many devices have been developed to indicate the level of hazardous gases for the protection of individuals and equipment but they all have several serious drawbacks. The present invention is designed to eliminate these drawbacks and to provide an apparatus that can remain in place without suffering the damaging effects of the harsh environment in which it is suspended.

Prior art sensing devices (the sensors) for the detection of hydrogen sulfide gas cannot ordinarily be continuously exposed to the gas or they will become saturated and loose the ability to function. This problem accounts for the need to have the prior art sensor devices located external to the gas environment, have a sampling tube with a pump mechanism to pump the atmosphere to be tested to the sensor, and then after the reading is made the sensor must be "aired out" to prevent saturation. This configuration limits the placement of prior art instruments to secure locations and the availability of power. Prior art comprising portable, hand held devices used for personal safety are limited to the lower limits of potential gas concentrations and are not capable of remaining in the sensing environment for long periods of time.

Examples of the prior art follow. The first is Wright, et al, U.S. Pat. No. 5,981,289 for a hydrogen sulfide analyzer that continuously samples waste water from a waste stream or reservoir and measures the concentration of purgeable hydrogen sulfide present. This information, when combined with the volume of water present, provides a control quality signal that regulates the feed rate of a destructor chemical into a waste stream. This results in chemical savings for the user. A second result is the reduction in odor complaints and the corrosion problems associated with hydrogen sulfide emissions. The analyzer measures only the purgeable hydrogen sulfide contained in the liquid sample. The analyzer violently agitates the sample containing dissolved hydrogen sulfide in solution to simulate actual conditions at points of agitation in the waste water stream. It also provides nearly optimal partial pressure conditions for the hydrogen sulfide to exit the solution as a free gas. Any hydrogen sulfide that does not come out of solution in the analyzer is not of interest to the user since it will most likely not come out of solution in the treatment process either. The analyzer controls the feed of the destructor chemical based upon the measured quantity and concentration of hydrogen sulfide that is likely to come out of solution in the collection/treatment process. It does not measure the total amount of sulfides present as other analyzers do. This is an important feature since it is wasteful to treat a condition that is not going to be a problem.

While Wright teaches a method of using a hydrogen sulfide sensor to determine the amount of a "destructor chemical" that should be released into an environment to mitigate the effect of the hydrogen sulfide, it does not address the problem of the continuous sampling's effect on the sensor's efficacy. The present invention improves this method by using clean air to purge the sensor, as well as has the ability to measure the amount of hydrogen sulfide in a gas, rather than in a liquid.

The next reference of interest is Church et al., U.S. Pat. No. 6,198,400 concerning portable gas detection and/or monitoring apparatus for a hostile environment. It includes a case having a substantially cylindrical wall and two opposite end caps sealably connected to the cylindrical wall, at least one of the end caps being removable from the cylindrical wall, and at least a portion of the cylindrical wall being transparent. A gas detection and/or monitoring unit is mounted in the case and includes gas-sensing means in sealed fluid communication with the ambient atmosphere outside the case. Data processing means is operatively connected to the gas sensing means, and data storage means and information display means is operatively connected to the data processing means. Calibrating means is operatively connected to the data processing means for calibration thereof to a predetermined gas concentration measured by the gas sensing means, the calibrating means including external switching means for selectively connecting the data processing means to the data storage means to allow transfer of data from said data storage means to said data processing means. Communication means is operatively connected to the data processing means or the data storage means for communicating data to the data processing means or the data storage means to an external destination and/or vice versa. A power supply is mounted in the case and operatively connected to the gas detection and/or monitoring unit and/or the gas sensing means.

Church teaches a suspension method for placing a sensing device in a hazardous environment, but it does not solve the problem of the saturation of the sensing device that renders it useless in a relatively short amount of time when placed in such a hazardous environment. The instant invention improves upon this teaching by solving the problem of saturation, by allowing the hazardous substance to only flow across the sensor membrane for a given amount of time and then flushing the membrane clean of detrimental particles. The present invention also does not include a housing having a transparent wall portion, and its switching means are internal, not external.

A further reference is Li, et al., U.S. Pat. No. 5,425,268 for water immersible vapor sensor. A continuous vapor sensor is disposed within a partially open protective enclosure which restricts (but does not exclude) the entry of liquid and means for excluding liquid from a portion of the enclosure, such as a non-wetting attachment material. The assembly allows the use of a continuous sensor which is adversely impacted by liquid contact in locations where the assembly may be immersed. The enclosure traps a sufficient amount of vapor to maintain a minimum vapor volume when the enclosure is submerged to a significant depth below a water level. The means for excluding controls the location of the minimum vapor volume to protect the sensor.

Li teaches that a sensor can be assembled to measure continuously vapor concentrations by drawing the vapor across the sensor. It is also taught that the sensor can communicate with an external recording device; however, the faults of such a system are highlighted in a hazardous environment, in which continuously exposed sensor equipment becomes desensitized, drastically reducing its efficacy and reliability. The instant invention fixes this problem by drawing in only the amount of sample necessary to take an accurate reading, and then purging the sensor of the harmful substance with clean air. Additionally, traditional means of communication with external devices are unable to operate when placed in hazardous environments such as in manholes.

Another reference is Novack, et al, U.S. Pat. No. 4,664,886 for a trimode gas detection instrument having three operating modes, one which monitors the level of combustible gases, a second which monitors oxygen, and a third which monitors the displacement of air by an unknown gas. Only two sensors are used, a combustible gas sensor and an oxygen sensor. A switch selects the input to a readout so that the user can quickly observe the concentration readings in any of the three modes. In the depletion mode the readout is calibrated in relation to the inverse of the normal concentration of oxygen in air, i.e., zero depletion corresponds to an oxygen concentration of 21%. In the event that an unknown gas displaces air in a sample atmosphere, concentration of the unknown gas appears on the readout, such that zero oxygen corresponds to a concentration of 100% unknown gas.

Novak teaches the use of a gas detection system that has three operating modes; each mode is initiated by an electronic method, through the use of a switch. The instant invention simplifies and improves upon Novak's concept by using a mechanical means to switch between positions on a three position valve, which is used to solve the sensor saturation problem previously described. Novak does not address the saturation of the sensor problem. The present invention's use of a mechanical method overcomes the problems caused by use in a hazardous or corrosive environment on electronic components. The present invention also solves the problem of using multiple sensors by employing just one sensor for gas detection.

An additional reference is Bell, et al., U.S. Pat. No. 5,010,021 concerning a method for restoring the sensing capacity of an electrical sensor. A selected component of a fluid mixture, for example a reduced sulfur compound vapor in air, is detected by selectively adsorbing the component onto a conductive thin layer of material having a chemical affinity for such component and observing the resultant change of electrical resistivity of the layer. The sensitivity of the detector changes with accumulation of the component on the sensor. The accumulation of the component on the sensor is removed by oxidizing and evolving the component from the sensor to restore the sensor to a linear operating region. The accumulated component is preferably oxidized by reacting the component with ozone. The dynamic range of the sensor is increased by counteracting the tendency for the component to accumulate by continuously feeding back ozone to or controlling the temperature of the sensor so that the sensor operates in a linear region near null.

Bell teaches a method for cleaning a sensor between testing through the use of oxidation. This method has the drawback that it uses a chemical means to decontaminate the sensor. The present invention uses a conditioned air source for decontamination, a preferred method compared to Bell due to the chemistry of the sensing device.

A final reference is Worth, et al, U.S. Design Pat. No. 432,037. It teaches the ornamental design for a gas detection unit which is cylindrical in shape. The present invention has rectilinear shape.

SUMMARY OF THE INVENTION

Bearing in mind the foregoing, it is a principal object of the present invention to provide an apparatus for the discrete sensing of gases in a harsh environment such as, but not limited to, hydrogen sulfide and other hazardous gases.

It is another object of the present invention to provide such a sensing capability that will operate on a continuing basis.

It is an additional object of the invention to provide an apparatus for the continuing discrete sensing of gases in a harsh environment which avoids the saturation of the sensor difficulties of the prior art.

It is related object of the present invention to provide for the communication of that sensing capability information remotely.

It is a further object of the present invention to provide all of the foregoing objects and advantages with an apparatus that can remain in place for an extended period of time without suffering damaging effects of the harsh environment in which it is suspended.

Other objects and advantages will become apparent to those skilled in the art upon reference to the following descriptions and the appended drawings.

In accordance with a principal aspect of the invention there is provided an apparatus for gas sampling from a harsh environment which comprises a chemically resistant plastic housing to which a chemically resistant plastic cover is attached and sealed using an internal o-ring. The housing is attached to a handle with a notch allowing the inventive apparatus to be suspended in a confined spacial environment. The housing has apertures for inlet and outlet tubes by which sampled air is drawn into and then discharged from the housing. Included are two three way solenoid valves to control selective fluid communication with the environment, a gas sensor disposed within the housing in selective fluid communication with the environment through the valves, a filter disposed within the housing to selectively remove contamination from the housing and prevent saturation of the gas sensor, a pump disposed within the housing to effect selective fluid flow through the gas sensor and filter, and a power source that is preferably batteries.

The apparatus electronics are all integrated into an electronics module on a PC board mounted within the housing under the cover and above the mechanical components, but clear of the battery compartment disposed at the bottom of the housing. These electronics are configured so as to communicate with an external readout in a remote location via several methods, such as, but not limited to, radio frequency (RF) exchange protocol wireless transmission, or by infrared (IR) radiation. The external readout is preferably a personal digital assistant (PDA). Sampling data is accumulated by a data logger included within the electronics module for transmission to the PDA. The data logger is comprised of a memory chip and includes the capacity to retain such information as date and time of sampling, concentration of each sample, and the unit's identification data. The electronics module is in electrical communication with the power source. Power is also supplied to the pump and valves that control the admission of sample gas, direction of it to the sensor, discharge of gas to the harsh environment, and filtration of all the atmosphere within the housing to (1) flush the sensor and (2) clear contamination from the interior of the housing.

The electronics module is operated by an integrated circuit microprocessor. The microprocessor controls timer functions, data logging functions, the opening and closing of valves and the operation of the pump. Depending on the concentration of the gas being monitored, the microprocessor is programmed to adjust the time of exposure of the sensor to the sample, and the time of the purge through the filter. Thus if one minute is the default sample exposure time and the sensor signal stabilizes after 30 seconds, the microprocessor will shut off the sampling, and begin the purge.

The sensor module is housed within its own chamber whereby the atmosphere to be sampled is drawn into the chamber from the harsh environment for the reading and then discharged from the chamber to allow clearing of the sensor to take place. This clearing allows the sensor to return to its baseline and prevents the saturation that is prevalent with the prior art.

The sampling and discharge of the atmosphere is accomplished by the air pump with attached pulsation damper acting as a vacuum pump by drawing the sample into the chamber and then discharging the sample air from the chamber. This is accomplished by the use of valves in the tubing lines as now described. These valves are three way valves, one being an inlet valve and the other being an outlet valve. Both valves are normally closed to the harsh environment, and both open to the harsh environment when energized. Sampling is initiated when both valves and the pump are energized, directing external gas flow through the inlet valve, through the pump, through the sensor and through the outlet valve back to the harsh environment.

The inlet valve is normally open to the interior of the housing, while the outlet valve is normally open to the filter inlet. When the pump is energized but neither valve is energized, gas contained within the housing goes through the inlet valve to the pump, is then pumped through the sensor, through the outlet valve, through the filter, and then is discharged back into the interior of the housing. The filter purges the gas being sampled from the housing to prevent saturation of the sensor as prevalent in the prior art because the sensor is able to return to baseline rapidly and consistently. The entire interior of the housing is purged of contamination from the sample gas.

That is, a crucial aspect of the present invention is that air disposed within the housing is drawn through a re-circulation flow path contained entirely within the housing using the pump to filter the sampled air in the sensor circuit and flush the sensor with air drawn from within the housing. All contaminated air is then passed through an absorbent filter and returned to the housing. The filter contains a zeolite-based chemically impregnated material for the purpose of absorbing the gas being monitored before returning the cleaned gas back into the housing.

In accordance with a second aspect of the invention, there is provided a method of operation of the apparatus that is critical to the nature of the invention and is required to achieve the desired result. The apparatus is designed with an electronics module that allows for two separate but interfaced timing circuits. These timers control the operation of the sampling pump and the valves. In use, the pump and valves are turned on simultaneously to begin the sampling procedure. After the sensor provides a stable reading both the inlet and outlet valves are closed to the harsh environment but the outlet valve directs the discharge from the sensor to the filter. The pump purges the sample from the sensor and continues to pump the contents of the housing through the filter until the sensor has returned to the baseline, and the interior of the housing is free of contamination. At this point the pump is turned off and the housing remains sealed from outside atmosphere. This completes one full cycle of the inventive apparatus. The timer then resets and the preprogrammed sequence begins to repeat this cycle discretely on a regular basis depending on the requirements of the environment and the data required to be collected. The data from the sensor is accumulated by the data logger along with the date and time and unit ID for future recall and analysis.

The apparatus can be used and the method practiced for extended periods in harsh environments, but periodically servicing of the apparatus is necessary. This usually requires battery and filter replacement, and the time interval between servicing is inversely proportional to the frequency with which samples are taken and the sampling time of each sample.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
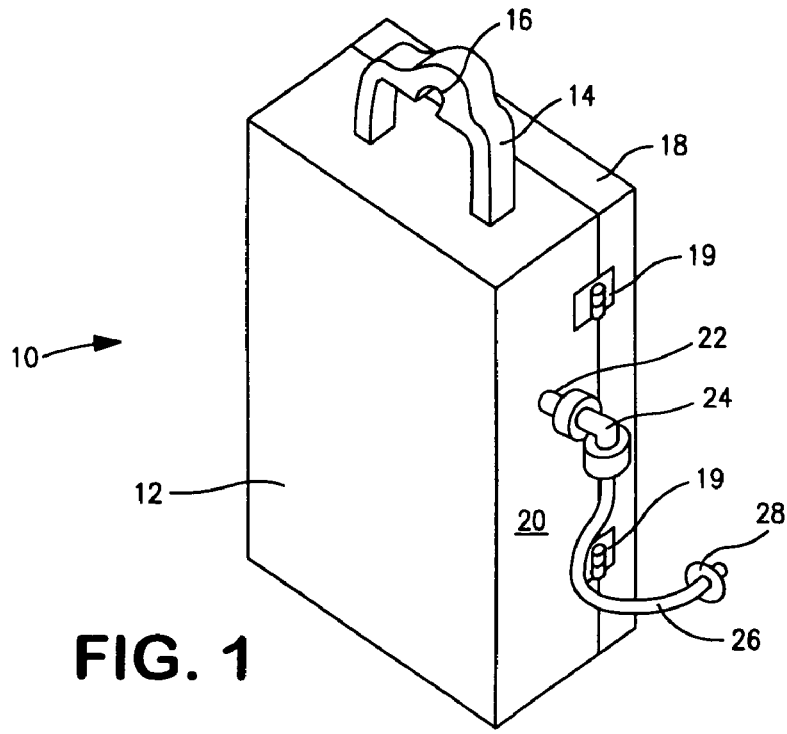
FIG. 1 is a perspective view of the invention showing the rectilinear windowless configuration of the housing and the sampling tube emanating from the housing sidewall.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

FIG. 1 is a prospective view of the invention 10. It includes a rectilinear, windowless housing having a rectangular footprint 12. It includes a carrying handle 14. Exposed at the top thereof is notch 16 allowing the inventive apparatus 10 to be suspended in a confined spacial hostile environment. The housing 12 includes a airtight cover 18. Penetrating the side 20 of housing 12 is an inlet tube 22 which is attached an elbow 24. The elbow 24 is in fluid communication with a sampling tube 26, to which is connected a sample fitting 28.

Figure 2:
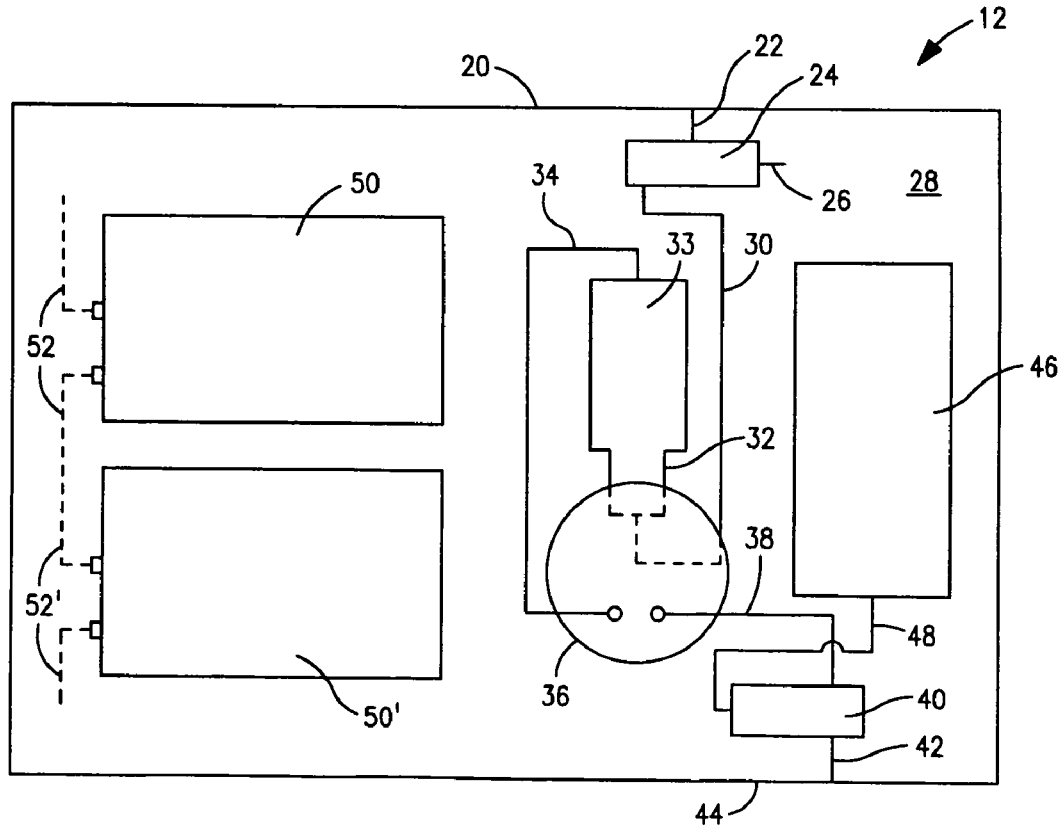
FIG. 2 is a schematic drawing of the preferred embodiment of the invention showing the principal components of the apparatus and their interrelationship.

FIG. 2 is a schematic plan view of the fluid components disposed within housing 12. Inlet tube 22 is shown connected to the aperture in side 20 and it is connected to a three-way valve 24 which includes alternate inlet 26. Alternate inlet 26 is open to the atmosphere 28 within housing 12. The outlet tube of three way valve 24 is 30. Outlet tube 30 is in fluid communication with pump 32 with attached pulsation damper 33. Pump discharge through tube 34 is in fluid communication with sensor 36. The sensor 36 in the preferred embodiment is designed to detect the presence and measure the concentration of hydrogen sulfide ($H_2S$). However, it is understood that other types gases can readily be detected and their concentrations measured using similar types of sensing devices that are both commercially available and readily suitable for use with the present invention.

Figure 3:
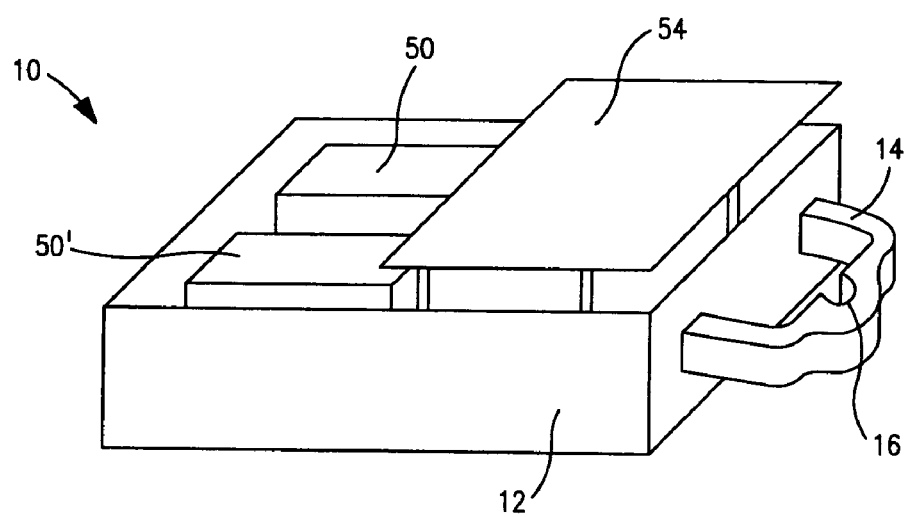
FIG. 3 is a perspective view of the housing with the cover removed and shows the location of the electronics module PC board 54 on top of the components described in regard to FIG. 2.

Sensor discharge tube 38 is in fluid communication with a second three-way valve 40 which in turn is in fluid communication with discharge tube 42 which penetrates side 44 of housing 12. Alternatively, three-way valve 40 fluid communication with filter 46 through filter inlet tube 48. Filter 48 is a cartridge which contains a zellite-based chemical impregnated material with the purpose of absorbing the hazardous chemical gas before returning the clean fluid back into the atmosphere 28 within housing 12. Batteries 50 and 50' are disposed in the lower half of the housing 12 with terminals with leads 52 and 52'. The leads are in electrical communication to the electronics module on a PC board 54 mounted within the housing under the cover and above the mechanical components, but clear of the battery compartment disposed at the bottom of the housing. See FIG. 3.

The electronics module as disposed on printed circuit board 54 provides for a plurality of functions. This includes electronic switches for switching the prompt on and off at predetermined intervals, switching the inlet and outlet solenoid valves on and off including implementation with an algorithm for reduced power mode while the valves are activated, data logging of each sample with a storage capacity for 60 days of sampling calculated at a maximum sample rate of 4 times per hour down to a minimum sample rate of once every six hours, with determination thereof based on the value of the previous sample, providing a real time clock with calendar and battery backup to time stamp samples and the like. The electronics module is designed to meet the requirements of UL Standard 913 Class I Division 1 Group C, D.

The specification include a user interface with LED's for low battery, cycle indication (IP 65 rating or similar) for zero sensor (pass/fail), calibrate sensor (pass/fail), magnetic switches for start unit, activate communications and for zero sensor, calibrate sensor, and system test. The $H_2S$ sensor is rated for a range of 5 to 1000 ppm, with an accuracy of plus or minus 5 ppm up to 50 ppm and plus or minus 10% of reading up to 1000 ppm with a sample frequency of 4 times per hour up to 200 ppm variable to one sample per hour at 1000 ppm. The sample time is for 3 minutes minimum with flow at 400 cc/min., sensor clearing 2 minutes pump time, monitor sensor baseline to operate the pump every 15 minutes for 1 minute, with a baseline suppression of 5 ppm in negative reading suppression. The battery pack will be supplied at 6 volts nominal, 5 volts low battery cutoff. Maximum current draw for the electronics modular and sensor is calculated at 25 mA.

The electronics module software is programmed to check for user input with manual and magnetic switches, maintaining time or functions, reading sensor voltage, converting sensor voltage to ppm, control of the solenoid valves, control of the air pump, reading the battery voltage, maintaining data logging functions, checking for download requests, and creating an output data file.

PC board 54 includes the power switch, magnetic start sample select switch and magnetic start communication select switch. It also includes functions for zero sensor select, calibrate sensor select, and system test select. Finally, it includes LED's for communications, low battery, sampling, zero sensor and calibrate sensor.

In accordance with a second aspect of the invention, there is provided a method of operation of the apparatus that is critical to the nature of the invention and is required to achieve the desired result. The apparatus is designed with an electronics module disposed on PC board 54 that allows for two separate but interfaced timing circuits. These timers control the operation of the sampling pump 32 and the valves 24, 40. In use, the pump 32 and valves 24, 40 are turned on simultaneously to begin the sampling procedure. After the sensor 36 provides a stable reading both the inlet 24 and outlet 40 valves are closed to the harsh environment but the outlet valve 40 directs the discharge from the sensor 36 to the filter 46. The pump 32 pushes out the sample from the sensor 36 and continues to pump the contents of the housing 12 through the filter 46 until the sensor 36 has returned to the baseline. At this point the pump 32 is turned off and the housing 12 remains sealed from outside atmosphere. This completes one full cycle of the inventive apparatus 10. The timer then resets and the preprogrammed sequence begins to repeat this cycle discretely on a regular basis depending on the requirements of the environment and the data required to be collected. The data from the sensor is accumulated by the data logger along with the date and time and unit ID for future recall and analysis.

The apparatus can be used and the method practiced for extended periods in harsh environments, but periodically servicing of the apparatus is necessary. This usually requires battery 50 and 50' and filter 56 replacement, and the time interval between servicing is inversely proportional to the frequency with which samples are taken and the sampling time of each sample.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. An apparatus for gas sampling from a harsh environment comprising:

a sealed housing compactly sized for deployment by suspension within the harsh environment of one of a manhole and wet-well of a sewage collection system;

a gas sensor disposed within the housing in selective fluid communication with the environment;

a filter disposed within the housing to selectively remove contamination from the housing and prevent saturation of the gas sensor;

a pump disposed within the housing to effect selective fluid flow through the gas sensor and filter; and two valves disposed within the housing controlling selective fluid communication with the environment, both valves being three way valves normally closed to the environment, but when energized allow gas to be sampled to flow into the apparatus through an inlet valve and tubing to the gas sensor, then through tubing and an outlet valve back out to the environment while keeping the housing interior otherwise contamination free, and when both valves are not energized the inlet valve is normally open to the contamination free atmosphere of the housing interior and the outlet valve is normally open to the filter such that the gas sensor can be purged of the gas being sampled to return to its baseline, while contamination is removed by being pumped through the filter rendering the complete housing interior contamination free.

2. The apparatus of claim 1 which further comprises an electronics module that is programmable to determine when both valves and the pump are energized to initiate gas sampling, when the sensor has reached a steady state concentration reading to shut both valves off, and when to shut off the pump after filtration has rendered the housing interior contamination free.

3. The apparatus of claim 1 which further comprises a data logger to retain gas concentration, date, time and unit ID information for retrieval at a location remote from the housing.

4. The apparatus of claim 3 that transfers stored data via means that include IR, wireless, and wired technology, and using a personal digital assistant at the location that is remote from the housing.

5. The apparatus of claim 1 where the gas is a toxic gas.

6. The apparatus of claim 1 where the gas is hydrogen sulfide.

7. The apparatus of claim 2 in which the electronics module further comprises software programmed to check for user input with manual and magnetic switches, maintaining time functions, reading sensor voltage, converting sensor voltage to ppm, switching solenoid valves on and off, control of the air pump, reading battery voltage, maintaining data logging functions, checking for download requests, and creating an output data file.

8. The apparatus of claim 7 in which switching the solenoid valves on and off includes implementation with an algorithm for reduced power mode while the valves are activated, data logging of each sample with a storage capacity for 60 days of sampling calculated at a maximum sample rate of 4 times per hour down to a minimum sample rate of once every six hours, with determination thereof based on a measured value of a previous sample, and providing a real time clock with calendar and battery backup to time stamp samples.

9. The apparatus of claim 1 that includes a power source that can be rechargeable batteries that are charged through one of conventional means and inductively.

10. The apparatus of claim 1 wherein the filter is a replaceable cartridge.

11. A method for gas sampling from a harsh environment comprising the steps of:

disposing a sealed housing compactly sized for deployment by suspension within the harsh environment of one of a manhole and wet-well of a sewage collection system;

energizing three way inlet and outlet valves and an air pump in fluid communication with a gas sensor all disposed within the housing to expose the gas sensor to gas brought into the sealed housing through the inlet valve from the environment being sampled and then discharged to the environment through the outlet valve;

de-energizing the three way inlet and outlet valves leaving the inlet valve normally open to a housing interior and the outlet valve normally open to a filter disposed within the housing;

pumping a fluid from the housing interior through the inlet valve through tubing to the gas sensor to purge it, fluid flow continuing through tubing to the outlet valve through tubing to the filter and back to the housing interior from a filter exit open to that interior, whereby the filter removes contamination from the housing and prevents saturation of the gas sensor; and shutting off the pump when the gas sensor has returned to its baseline.

12. The method for gas sampling of claim 11 which further comprises timing out a next sampling cycle based on a measured concentration of gas from a preceding sampling cycle.

13. The method for gas sampling of claim 12 which further comprises storing the measured concentration of gas in a data logger with date, time and unit ID information for retrieval at a location remote from the housing.

14. The method for gas sampling of claim 13 which further comprises retrieving of the data stored in the data logger at the location that is remote from the housing.

15. The method for gas sampling of claim 14 that includes remotely retrieving stored data via means that include IR, wireless, and wired technology, and using a personal digital assistant at the location that is remote from the housing.

* * * * *